United States Patent [19]

Yoon

[11] Patent Number: 5,047,047
[45] Date of Patent: Sep. 10, 1991

[54] WOUND CLOSING DEVICE

[76] Inventor: InBae Yoon, 2101 Highland Ridge Dr., Phoenix, Md. 21131

[21] Appl. No.: 508,593

[22] Filed: Apr. 13, 1990

Related U.S. Application Data

[63] Continuation-in-part of Ser. No. 262,980, Oct. 26, 1988, Pat. No. 4,924,866.

[51] Int. Cl.⁵ .............................................. A61B 17/00
[52] U.S. Cl. ..................................... 606/216; 606/213
[58] Field of Search ............... 606/213, 214, 215, 216, 606/220, 221

[56] References Cited

U.S. PATENT DOCUMENTS

| | | |
|---|---|---|
| 3,487,836 | 1/1970 | Niebel et al. |
| 3,825,010 | 7/1976 | McDonald ........................ 606/216 |
| 4,430,998 | 2/1984 | Harvey et al. ..................... 606/216 |
| 4,526,173 | 7/1985 | Sheehan ............................ 606/216 |
| 4,539,990 | 9/1985 | Stivala . |
| 4,637,380 | 1/1987 | Orejola ............................. 606/216 |
| 4,676,245 | 6/1987 | Fukuda ............................. 606/216 |
| 4,702,251 | 10/1987 | Sheehan . |

Primary Examiner—Stephen C. Pellegrino
Assistant Examiner—Gary Jackson

[57] ABSTRACT

A wound closing device includes a body having first and second arms interconnected to allow relative angular movement therebetween, and at least one skin-engaging member carried by each arm the body having a closed position where free ends of the skin-engaging members are moved toward each other to penetrate skin surround the wound. The wound closing device can be integrally formed from a strip of bendable material to urge the arms to the closed position, and the arms are movable to an open position to space the free ends of the skin-engaging members to span the wound. The skin-engaging members can be hollow to introduce medication into a wound and can have various configurations, spacing and dimensions dependent upon the wound to be closed.

43 Claims, 3 Drawing Sheets

WOUND CLOSING DEVICE

The application is a continuation-in-part of pending application Ser. No. 07/262,980 filed Oct. 26, 1988 now U.S. Pat. No. 4,924,866.

BACKGROUND OF THE INVENTION

1. Field of the Invention

The present invention pertains to devices for closing wounds and, more particularly, to devices for replacing stitches and staples for closing wounds.

2. Discussion of the Prior Art

The most widely used method for closing skin wounds are passing a suture through the skin to approximate the edges of the skin and hold the skin stitched in place for healing. Suturing or stitching has the advantage of allowing the physician to adjust tension and, therefore, approximation on a stitch by stitch basis but also has the disadvantages of being labor intensive, time consuming, requiring manual dexterity on the part of the physician in order to close the wound in such a manner as to minimize scarring and also requiring removal of the stitches, usually necessitating an additional visit to the physician.

In order to reduce the time and labor required for suturing, many physicians use staples; however, staples have the disadvantages of requiring special equipment, of requiring removal and being difficult to remove, of requiring a special instrument for removal and, most importantly, depriving the physician of the adjustable approximation and tension obtained from suturing.

Other devices for closing wounds are disclosed in the prior art. For example, U.S. Pat. No. 3,487,836 to Niebel, et al discloses a surgical strip stitch wherein an inverted U-shaped member has flexible adhesive strips attached on the extremities thereof for attachment to the skin on either side of a wound bridged by the U-shaped member. Skin-engaging projections extend inwardly from each side wall of the U-shaped member and have blunt end portions adapted to clamp the edges of a wound together in a peak therebetween. U.S. Pat. Nos. 4,526,173 and 4,702,251 to Sheehan disclose skin closure devices formed of a pair of attachment members adapted to be positioned along either side of a wound to be closed. In one embodiment, the device includes a plurality of pins associated with the attachment members for the purpose of urging the dermis on either side of the wound together. In another embodiment, a bridge is provided to hold the two attachment members in abutting alignment to close a wound. U.S. Pat. No. 4,539,990 to Stivala discloses a sutureless closure system having fabric-backed plates positioned along the side edges of a wound. Arcuate shaped clips bridge the wound between the plates and contain downwardly extending pins at each end to penetrate the fabric, not the skin, to form a secure anchor for the bridge.

The prior art attempts to produce wound closing substitutes for conventional suturing, as discussed above, thus have reduce the time and labor required to close a wound but have failed to produce the precision skin approximation necessary to minimize scarring. Other disadvantages of the prior art include high cost, difficult removal, requirement of complex devices and concomitant difficult application and not being easily usable in emergencies.

SUMMARY OF THE INVENTION

Accordingly, it is a primary object of the present invention to provide a wound closing device overcoming the above mentioned disadvantages of the prior art.

Another object of the present invention is to provide a closing device of simple, inexpensive construction which can be easily manipulated by a physician or persons with minimal medical training.

It is a further object of the present invention to provide wound closing devices having structure to permit use for closing various shapes and locations of wounds to minimize formation of scar tissue during healing.

It is a still further object of the present invention to provide a wound closing device which can be easily removed by medical personnel or patients manually without the need for special instruments.

An additional object of the present invention is to dispose a bandage at the interconnection of a pair of arms of a wound closing device wherein each of the arms carries at least one skin-engaging member for penetrating skin on opposite sides of a wound such that the bandage overlies the wound.

A further object of the present invention is to use a wound closing device to close a wound and also to protectively cover he wound with or without a bandage covering a central portion of the wound closing device or the entire wound closing device.

The present invention has another object in the use of curved skin-engaging members extending from arms of a wound closing device such that each of the skin-engaging members follows a single path when penetrating the skin and when being removed from the skin.

An additional object of the present invention is maximize closure of wounds of various size, shape and depth at various locations in skin of varying texture by using various configurations and spacing of skin-engaging members to assure the skin being securely held in place.

Yet a further object of the present invention is to construct a wound closing device to angularly urge opposing arms carrying skin-engaging members toward a closed position such that the skin-engaging members are urged toward each other to approximate opposing edges of a wound with a desired tension.

Another object of the present invention is to construct a wound closing device of a strip of spring-like material to urge opposing arms of the wound closing device toward each other to approximate opposing edges of a wound.

Some of the advantages of the wound closing device of the present invention over the prior art are that the wound closing device produces more precise edge to edge approximation of the wound, the wound closing device covers and protects the wound site, the use of a plurality of skin-engaging members each arm of the wound closing device decreases wound closure time, the wound closing device can be combined with a strip bandage with or without medicated gauze, the wound closing devices are individually adjustable to produce variable tension of skin approximation producing the desired tension for wounds having irregular edges such as edge configurations resulting from skin resection, with the use of hollow or needle-like skin-engaging members on the wound closing device medication can be introduced under the skin for wound healing, the wound closing device can be accurately used in emergencies by untrained personnel, the wound closing device is less expensive than skin staplers, is simpler and safer to use with less chance of infection, provides protective cover for the wound closure site, and produces more precise approximating, better healing and less scarring, subcutaneous approximation is not required when the wound closing device has long pairs of skin-engaging members carried by the opposing arms, the wound closing device can be used on both deep and shallow wounds and small puncture wounds such as those made during endoscopy procedures, the wound closing device can have adhesive on the underside or can be used with adhesive tape or strip bandages, the wound closing device can be coated with healing-facilitating agents, such as anaesthetic, antiseptic agents or anti-keloid or long term medications, and the wound closing device can be used in a wide range of surgical procedures including pediatric and plastic surgery.

The present invention is generally characterized in a wound closing device including first and second arms having inner ends interconnected to allow relative angular movement therebetween, at least one skin-engaging member carried by each arm and means urging the arms toward a closed position where free ends of the skin-engaging members are moved toward each other to penetrate skin surrounding the wound. The wound closing device can be integrally formed from a strip of spring-like material to urge the arms to the closed position, and the arms are movable to an open position to space the free ends of the skin-engaging members to span the wound. The skin-engaging members have various configurations, spacing and dimensions dependent upon the wound to be closed; and, by providing the skin-engaging members with curved configurations, each of the skin-engaging members follows a single path when penetrating the skin and being removed from the skin. A bandage can be disposed at the interconnection between the arms to overlie the wound and, if desired, carry a medicament; and, by using hollow skin-engaging members, medicaments can be subcutaneously introduced into the wound with the wound closing device in place.

Other objects and advantages of the present invention will become apparent from the following description of the preferred embodiment taken in conjunction with the accompanying drawings.

DESCRIPTION OF THE PREFERRED EMBODIMENTS

Figures 1, 2, 3, 4, 5:
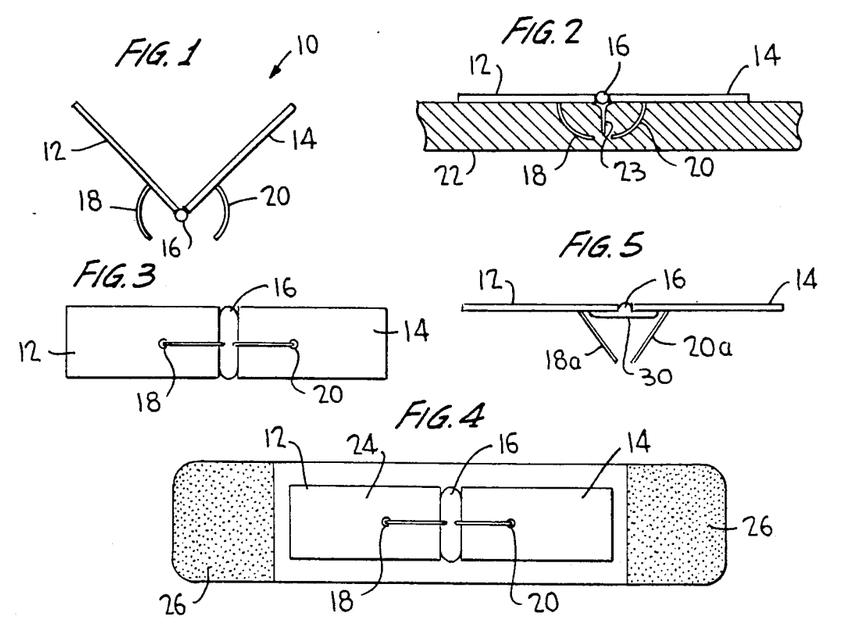
FIG. 1 is a side view of a wound closing device according to the present invention in an open position.
FIG. 2 is a side view of the wound closing device of FIG. 1 in a closed position over a wound.
FIG. 3 is a bottom view of the wound closing device in the closed position.
FIG. 4 is a bottom view of another embodiment of the wound closing device in its closed position.
FIG. 5 is a side view of a further embodiment of the wound closing device in the closed position.

A wound closing device 10 in accordance with the present invention is shown in an open position in FIG. 1 and includes a bendable body formed of a first arm 12 and a second arm 14 pivotally connected at the inner ends thereof by a joint 16. A skin-engaging member 18 is affixed to arm 12, and a skin-engaging member 20 is affixed to second arm 14. In the open position shown in FIG. 1, arms 12 and 14 are pivoted or angularly moved upwardly out of the same plane to the open position wherein the skin-engaging members 18, 20 are separated from one another.

The joint 16 may incorporate a spring of any suitable type therein functioning as an over-center type spring to urge the arms 12, 14 to the open position when the arms are moved a predetermined distance toward the open position and also functioning to urge the arms 12, 14 to the closed position when the arms are moved a predetermined distance toward the closed position. Alternatively, the spring may be constructed to urge the arms 12, 14 to the closed position only. The joint 16 may also be formed of a malleable material so that the arms 12, 14 can be moved to and held in the open or the closed position.

The wound closing device is shown in the closed position in FIG. 2 such that skin 22 is pinched together or approximated by skin-engaging members 18, 20 to close wound 23. As shown, skin-engaging members 18, 20 penetrate the skin 22 on opposite sides of wound 23. Skin-engaging members 18, 20 are preferably shaped to extend downwardly and inwardly to pinch together and penetrate skin 22 around wound 23 when the wound-closing device is in the closed position. The skin-engaging members are curved downwardly and inwardly as shown in FIGS. 1 and 2. In the closed position, the free ends of skin-engaging members 18, 20 are in close proximity to one another as shown in FIG. 2. The free ends of skin-engaging members 18, 20 may also physically touch one another in the closed position if desired. Skin-engaging members 18, 20, thus, securely and accurately hold the edges of the wound together with desired tension to promote fast healing with minimal formation of scar tissue. Accuracy of the edge-to-edge skin approximation is improved due to the flattening of the skin by the body of the wound closing device as well as the bias of the skin-engaging members toward each other.

As illustrated in FIG. 3 arms 12, 14 preferably are planar, generally rectangular members. Arms 12, 14 may be fabricated from any suitable thin metal or plastic material, although any other medically acceptable material will suffice. Arms 12, 14 are generally rectangular, planar members in the preferred embodiment to make the device easier to handle during use and operation. Arms 12, 14 have a length to be easily grasped by a hand for opening and closing the wound closing device and have a width such that several wound closing devices can be used side-by-side to close a large wound and so that a number of wound closing devices can be placed in close proximity to one another to satisfactorily close a wound, when necessary. The wound closing device may include more than one skin-engaging member 18, 20 attached to each arm dependent upon the wound to be closed.

The joint 16 may be any medically approved type of spring device or mechanical means for biasing or engaging the arms 12, 14 to the closed position and, if desired, to the open position. Joint 16 may also be a bendable spring joint and may be fabricated from plastic or other suitable material as an integral part of arms 12, 14. Joint 16 can also be fabricated separately from arms 12, 14 and suitably attached thereto. The spring force should be sufficient to hold the edges of a wound in close engagement when the wound closing device is positioned thereon in a closed position to promote wound healing with a minimum of scar tissue. When joint 16 urges the arms 12, 14 only to the closed position, manual force is necessary to open the arms 12, 14 and hold them in the open position while the wound closing device is applied to a wound. Release of the arms results in the arms being closed to cause the skin-engaging members 18, 20 to penetrate the skin adjacent the wound, as shown in FIG. 2.

Skin-engaging members 18, 20 can be fabricated from any suitable, medically acceptable material, such as plastic, Teflon, rubber or metal, for example, and can have various shapes, sizes and orientation depending upon the particular wound to be closed. For example, for larger wounds, skin-engaging members 18, 20 will be longer and will be attached to arms 12, 14 further from joint 16 so that the skin-engaging members 18, 20 will span the large wound. To accommodate a smaller wound, skin-engaging members 18, 20 will be shorter and attached to arms 12, 14 closer to joint 16. The skin-engaging members 18, 20 preferably have curved configurations as shown in FIGS. 1 and 2 with centers at joint 16 such that each skin-engage member travels in a single path during both penetration and removal. Other shapes may also be used such as, for example, angled members having two straight sections which form an acute angle therebetween with the free ends positioned inwardly for engagement and penetration of the skin around a wound. Also, straight members 18, 20 can be used as shown in FIG. 5. The free ends of skin-engaging members 18, 20 have relatively sharp points to facilitate penetration of the skin around the wound. Penetration of the skin by the skin-engaging members 18, 20 exerts a pinching effect on the skin around the wound to bring the edges of the wound into close proximity facilitating healing and minimizing formation of scar tissue.

In FIG. 2, arms 12, 14 are shown in the same plane in the second, closed position; however, the angle between arms 12, 14 in the closed position will vary for different applications. For example, to close a wound in the forearm of a patient, the wound closing device will be fabricated such that arms 12, 14, in the closed position, follow the contour of the patient's arm, either by having curved arms 12, 14 or by selecting joint 16 so that arms 12, 14 form an angle less than 180° between one another. The angle between arms 12, 14 in the closed position is preferably from about 170° to about 190° and more preferably about 180°, although for specific applications, larger or smaller angles may be used. Accordingly, it is contemplated that a wide variety of wound closing devices may be provided such that the correctly configured device or devices can be chosen for the particular wound to be closed. The devices will vary in both the angle of the arms 12, 14 to one another as well as the size, number and positioning of skin-engaging members 18, 20, depending upon the type and location of the wound.

In operation of the wound closing device where the joint 16 has a spring device that urges the arms 12, 14 to the open and the closed positions, the wound closing device is picked up in the open position as shown in FIG. 1 and is positioned such that skin-engaging members 18, 20 straddle the wound to be closed with one hand, and the other hand is used to grasp on either side of the wound and pinch the skin together to close the wound. The wound closing device is then moved toward the closed position so that the spring device urges the arms 12, 14 to the closed position wherein skin-engaging members 18, 20 penetrate the skin on either side of the wound and pinch the wound closed. Arms 12, 14 will act as a barrier to help secure the skin and close the wound. As shown in FIG. 2, the skin is pinched by skin-engaging members 18, 20 and impinges against arms 12, 14 as well. If the spring device urges the arms 12, 14 only to the closed position, the operation is similar except that the wound closing device is picked up in the closed position and manually moved to the open position before application to the wound.

To remove the wound closing device, the free ends of arms 12, 14 are moved upwardly to withdraw skin-engaging members 18, 20 from the skin, and the wound closing device is removed from the site of the wound and may be discarded.

Another embodiment of the wound closing device is shown in FIG. 4 wherein a bandage is attached in any suitable manner to the upper portion of the body of the wound closing device to provide additional protection for the wound. The bandage includes a wound-covering portion 24, preferably made of gauze or other suitable material, and a pair of adhesive end portions 26. Preferably, wound-covering portion 24 is secured to the top surface of arms 12, 14. Adhesive portions 26 provide additional means for retaining the wound closing device on the patient's skin, and wound-covering portion 24 provides additional protection to the wound area from dirt and other contaminating materials. The end portions 26 or other portions of the bandage may be formed of a flexible and resilient material so that the bandage can be stretched before being applied to the wound area to provide an additional closing force to the wound.

In another embodiment, wound-covering portion 24 and/or the bottom portions of arms 12, 14 may include a medicament. The medicament may be any known medical substance suitable for the healing of a wound, the prevention of infections or the lessening of pain.

Such a medicament could also be applied to the skin-engaging members 18, 20.

Referring to FIG. 5, a pad 30, such as a bandage or gauze, is disposed at the interconnecting joint 16, and adjacent portions of the arms 12, 14 can be impregnated or coated with a suitable medicament such as an antiseptic, an anaesthetic, a pain-killing agent or a specific anti-keloid agent. In FIG. 5, skin-engaging members 18a and 20a are shown having straight, inwardly directed configurations as another example of the shape of such members in accordance with the invention.

The bottom surfaces of the arms 12, 14 can be provided with an adhesive of any suitable type to aid in retaining the wound-closing device on the skin in the proper closed position around the wound.

Figure 6:
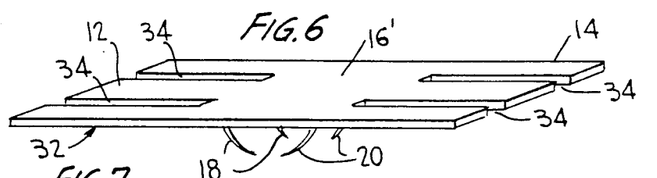
FIG. 6 is a perspective view of another embodiment of a wound-closing device according to the present invention.
Figure 7:
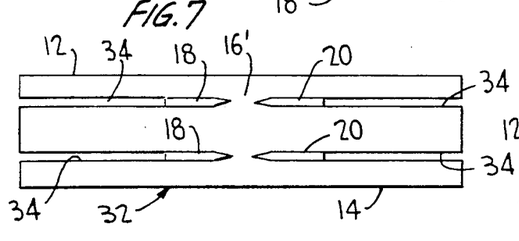
FIG. 7 is a bottom view of the wound closing device of FIG. 6 in the closed position.
Figure 8:
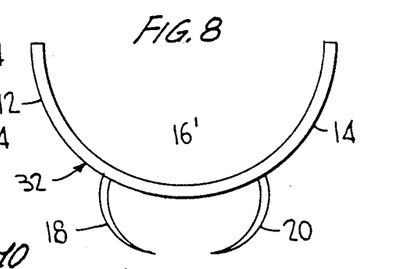
FIG. 8 is a side view of the wound closing device of FIG. 6 in the open position.

As discussed above, the arms and the joint of the wound closing device of the present invention can be integrally formed, and such an integrally formed embodiment is shown in FIGS. 6, 7 and 8 wherein the arms 12 and 14 are interconnected at their inner ends by a portion 16' serving the same function as joint 16, that is, to allow the arms to angularly move or bend thereabout between the open and closed positions. The wound closing device body formed of arms 12, 14 and portion 16' is integrally formed of a single strip of material 32 having bendable, spring-like properties, such as plastic, metal or rubber, with the strip of material normally being in the closed position shown in FIGS. 6 and 7 such that the free ends of the skin-engaging members 18 and 20 are urged toward each other to hold the skin or tissue in closely abutting relation for healing. The strip of material 32 can be formed with slots 34 therein, and the material from the slots can be bent down with a curved configuration to form skin-engaging members 18 and 20. Accordingly, the wound-closing device can be inexpensively formed by a metal stamping process, if desired. As mentioned above, more than one skin-engaging member can extend from each arm; and, accordingly, each arm of the wound-closing device of FIGS. 6, 7 and 8 is shown carrying two skin-engaging members for exemplary purposes.

The operation of the wound-closing device of FIGS. 6, 7 and 8 is similar to that described above, it being appreciated that interconnecting portion 16' allows similar angular movement of the arms thereabout as does joint 16. Since the strip of material is normally in the closed position shown in FIGS. 6 and 7, force must be applied to the arms to overcome the spring or memory properties of the strip of material to move the arms to the open position shown in FIG. 8 such that the free ends of the skin-engaging members can span a wound. When the arms are released, the arms will be spring biased back to the closed position urging the skin-engaging members into the skin and toward each other.

Figure 9:
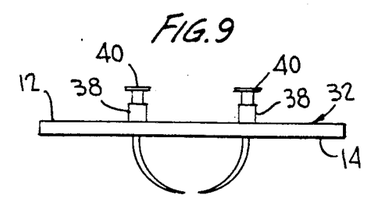
FIGS. 9 and 10 are side views of a further embodiment of a wound closing device according to the present invention having hollow skin-engaging members in the closed and open positions, respectively.
Figure 10:
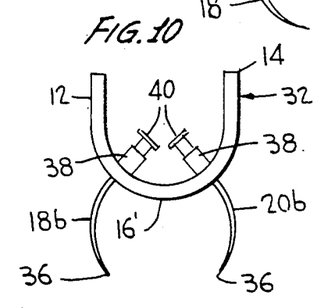

A further embodiment of a wound closing device according to the present invention is shown in FIGS. 9 and 10 and includes hollow, needle-like skin-engaging members 18b and 20b having open free ends 36 and terminating proximally at open hubs 38 closed by removable caps 40. The hubs and caps function to limit bending movement to the open position due to abutment of the caps as shown in FIG. 10. Should the wound become infected after application of the wound closing device, the caps 40 can be removed, and medication can be introduced subcutaneously via syringes received in hubs 38. Additionally, with the use of hollow skin-engaging members continuous medication can be supplied to the wound as the skin heals. While the hubs 38 are shown protruding above the strip of material 32, the hollow skin-engaging members can terminate flush with the strip of materials. If desired, a medicated sponge or gauze can be disposed at interconnection 16' to overlie the wound and further supply medication thereto.

Figure 11:
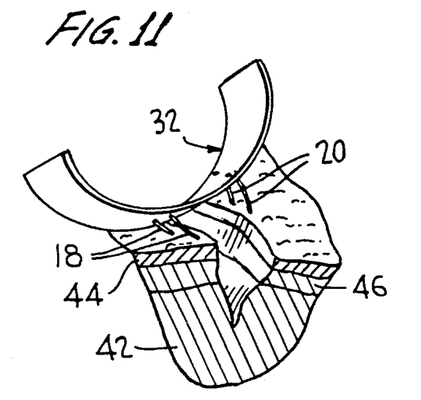
FIGS. 11, 12, 13 and 14 are broken sectional views of various size wounds with wound closing devices having skin-engaging members of varying lengths to accommodate the wounds.
Figure 12:
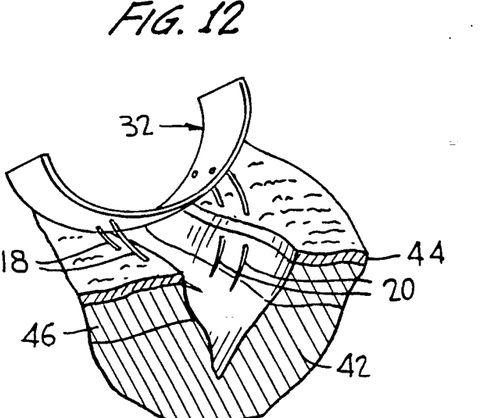
Figure 13:
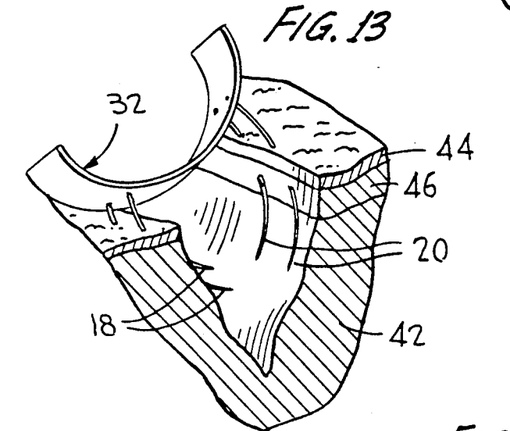
Figure 14:
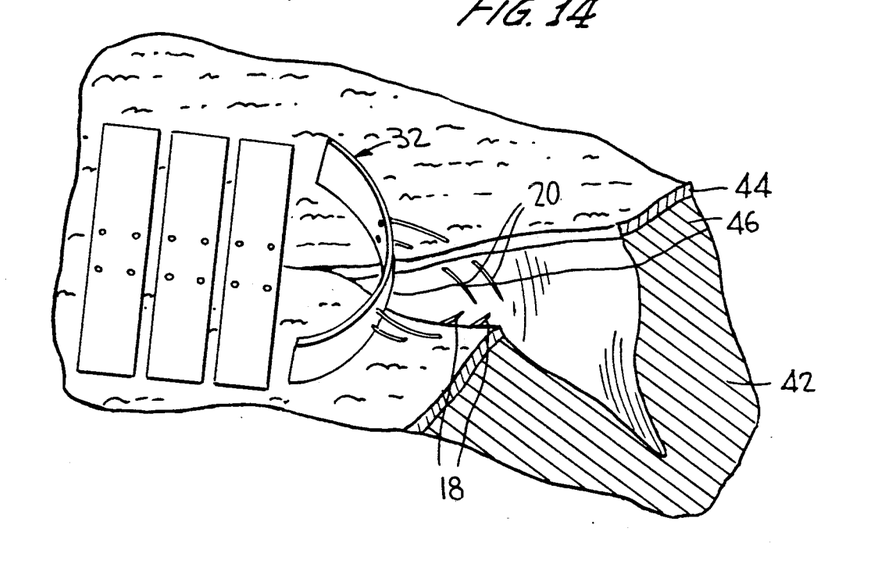

Skin is formed of an epidermis layer overlying the dermis which overlies a subcutaneous or fatty layer, and progressively deeper wounds are shown in FIGS. 11, 12 and 13, all extending into the subcutaneous layer 42. Since the wound shown in FIG. 11 is not as deep as the wound shown in FIG. 12, a wound closing device having shorter skin-engaging members is utilized than the wound closing device shown in FIG. 12. Similarly, the skin-engaging members of the wound closing device shown in FIG. 13 are longer than those shown in FIG. 12. By selecting a wound closing device having skin-engaging members of the proper length and configuration, the various size wounds can be closed with adjustable approximation without additional approximation of the subcutaneous layer. That is, the skin-engaging members 18, 20 pass through the epidermis 44, the dermis 46 and sufficiently into the subcutaneous layer 42 to allow approximation of all layers simultaneously as the wound closing device is moved to the closed position. FIG. 14 shows the use of a plurality of wound closing devices to close a wound while simultaneously protectively covering the wound, it being appreciated that the wound closing devices will each have a configuration optimal for the portion of the wound closed thereby. By varying the size, length, configuration of the skin-engaging members, the wound closing device of the present invention can be used to close virtually all types of wounds with adjustable approximation and tension so long as the free ends of the skin-engaging members are urged toward each other in the closed state. The wound closing device of the present invention produces excellent healing and is also simple and quick to apply thus saving time and being extremely effective where time is of the essence, such as in emergency situations. By combining medicated bandages or pads, the wound closing device is particularly effective, and supply of medication through the hollow skin-engaging members allows treatment of a wound not previously available. The wound closing device can be packaged in sterile form in removable paper similar to strip-type bandages.

The wound-closing device of the present invention has the size and configuration of a conventional strip-type bandage and can be applied in a simple manner while facilitating healing and minimizing scarring. The skin-engaging members can have any desired configuration with the free ends thereof directed toward each other, and the use of curved or arcuately configured skin-engaging members is particularly advantageous in that the entire length of the skin-engaging members pass along a single path reducing trauma and promoting healing. The strip of material from which the wound closing device is formed can be transparent to permit observation of the wound, and the strip of material can carry medication, if desired.

As discussed above, the skin-engaging members can have various configurations dependent upon the wound to close. Accordingly, while the curved skin-engaging members produce minimal trauma, the curved skin-engaging members also can be inadvertently dislodged.

Figure 15:
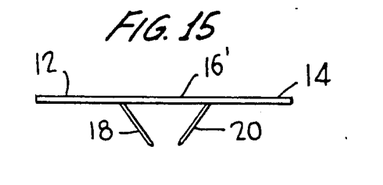
FIGS. 15 and 16 are side views of another embodiment of a wound closing device according to the present invention in closed and open positions, respectively.
Figure 16:
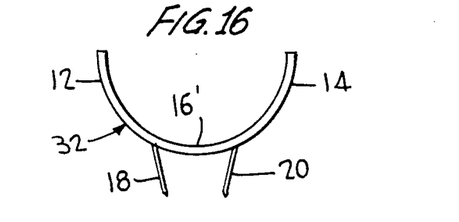

FIG. 15 shows straight, inwardly directed skin-engaging members 18 and 20 extending from opposing arms 12 and 14 of strip of bendable material 32 in the closed position, while the open position is shown in FIG. 16 wherein it can be seen that the skin-engaging members are positioned substantially transverse to the skin around the wound facilitating penetration. After penetration, return of arms 12 and 14 to the closed position moves the skin-engaging members toward each other.

Figure 17:
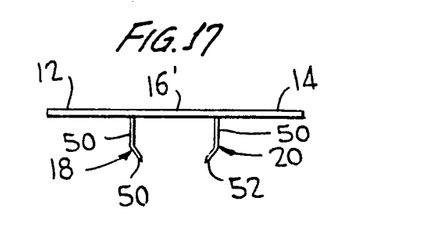
FIGS. 17 and 18 are side views of another embodiment of a wound closing device according to the present invention in closed and open positions, respectively.
Figure 18:
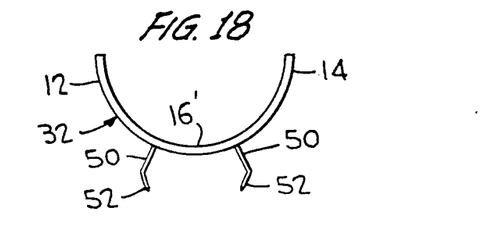
Figure 19:
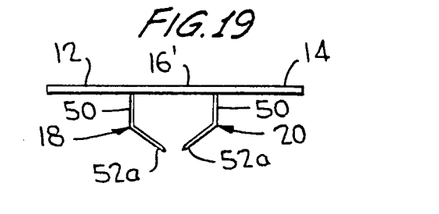
FIGS. 19 and 20 are side views of another embodiment of a wound closing device according to the present invention in closed and open positions, respectively.
Figure 20:
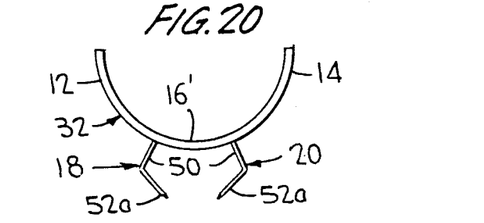
Figure 21:
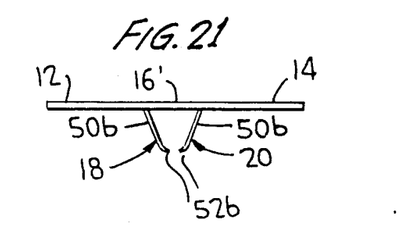
FIGS. 21 and 22 are side views of another embodiment of a wound closing device according to the present invention in closed and open positions, respectively.
Figure 22:
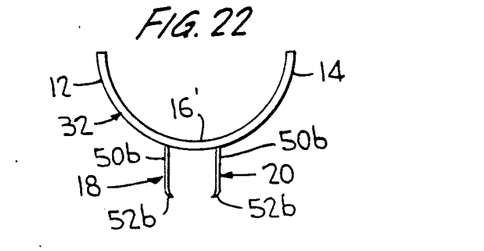

FIGS. 17, 19 and 21 show configurations of skin-engaging members 18 and 20 having sharp free ends extending angularly from legs extending from the opposing arms 12 and 14 to lock or anchor the skin-engaging members in the skin. More particularly, the skin-engaging members 18 and 20 of the embodiment of FIG. 17 each include a leg 50 extending transversely from a respective arm and a sharp free end 52 extending angularly therefrom toward each other and the interconnecting intermediate portion 16'. When the wound closing device is in the open position shown in FIG. 18, the free ends 52 will be widely spaced and, after return to the closed position, the angled free ends 52 will lock the skin-engaging members in the skin. The embodiment of FIG. 19 is similar to FIG. 17 with the exception that angled free ends 52a are longer producing increased locking in the skin and decreased space therebetween in the open position, as shown in FIG. 20. The embodiment of FIG. 21 has inwardly angled legs 50b with very short angled free ends 52b such that, in the open position shown in FIG. 22, the skin-engaging members penetrate the skin substantially transversely. It will be appreciated from the above, that by selecting the proper configuration of skin-engaging members and spacing and size thereof for each particular wound site, extremely accurate and precise wound closing can be accomplished. For example, the embodiment of FIG. 19 is particularly advantageous at constantly moving wound sites, such as the knee, and at sites requiring tighter approximation and more tension, such as keloid areas and areas with removed skin or irregular shape. The embodiment of FIG. 17 is particularly advantageous for wounds requiring only loose approximation and, in some cases, the angled free ends are not required. Where the skin-engaging members extend transverse to the arms, removal of the wound closing device is facilitated allowing simple straight out removal by a patient. The closer the spacing between skin-engaging members, the more accurate the skin approximation. By providing pairs of skin-engaging members on each arm, symmetrical approximation is enhanced while minimizing skewing of the wound closing device.

Figure 23:
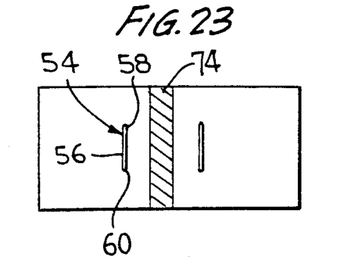
FIGS. 23, 24 and 25 are top plan views of wound closing devices according to the present invention illustrating arrangements for securing the skin-engaging members to the body thereof.
Figures 24, 25:
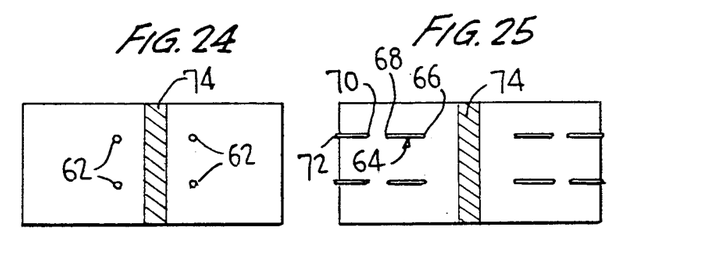

FIGS. 23, 24 and 25 show arrangements for mounting the skin-engaging members on the arms when the skin-engaging members are not integral with the body as shown in FIGS. 6, 7 and 8. In FIG. 23, the pair of skin-engaging members for each arm are made of a wire 54 having sharp ends and a U-shape with a base 56 lying along each arm and the legs 58 and 60 extending through holes in the arms. In FIG. 24, the proximal ends 62 of the skin-engaging members are secured in holes in the arms. In FIG. 25, each skin-engaging member is formed of a wire 64 threaded through holes 66, 68 and 70 and wrapped around the ends of the arms to have a serpentine configuration hooked at one end 72 on the end of an arm and having an opposite end forming the skin-engaging member. The skin-engaging members can be secured in any conventional manner such as welding, gluing, swaging or the like.

Also shown in FIGS. 23, 24 and 25 are alignment stripes 74 extending laterally, centrally across the wound closing device bodies which serve to provide a guide during application of the wound closing device. As described above, the wound closing device can be transparent which allows viewing of the wound during application; and, where the wound cannot be seen, stripe 74 allows alignment with the wound and with adjacent wound closing devices. The stripes can also serve to identify the various wound closing device configurations by color coding.

Figure 26:
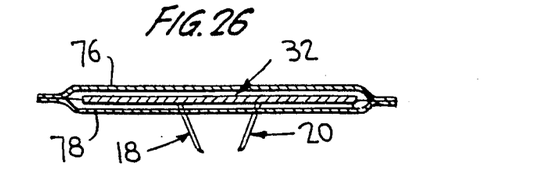
FIG. 26 is a sectional view of a wound closing device according to the present invention of laminar construction.

The embodiment of FIG. 26 shows a wound closing device as previously described covered or laminated by layers 76 and 78 of medical grade material to give the wound closing device the appearance of a strip-type bandage, the layers being sealed at their edges with skin-engaging members 18 and 20 penetrating through layer 78. The wound closing devices, with or without lamination, are provided in sterile condition in wrappers to be ready for use once the wrapper is removed.

While various embodiments of the present invention have been shown and described, it is preferred to construct the wound closing device of a strip of bendable material, such as metal, plastic or rubber, to be movable between open and closed positions. When the bendable material has spring-like properties, the skin-engaging members are urged toward each other to hold the skin edges in approximation. The flat underside of the strip flattens the skin at the wound site to facilitate precise healing and to protectively cover the wound. By stamping or injection molding, the strip can be inexpensively made; however, as described above, the angular movement of the opposing portions of the wound closing device body, referred to herein as arms, can be provided by bodies formed of a plurality of connected parts.

Inasmuch as the present invention is subject to many variations, modifications and changes in detail, the above description of the preferred embodiments is intended to be exemplary only and not limiting.

What is claimed is:

1. A wound closing device comprising
   a first arm having an inner end and an outer end and carrying at least one skin-engaging member extending from said first arm at a position between said inner and outer ends and having a free end for penetrating the skin;
   a second arm having an inner end and an outer end and carrying at least one skin-engaging member extending from said second arm at a position between said inner and outer ends and having a free end for penetrating the skin;
   means interconnecting said inner ends of said first and second arms for allowing angular movement thereof relative to each other between an open position where said free ends of said first and second arm skin-engaging members are spaced from each other to span a wound and a closed position where said free ends of said first and second arm skin-engaging members are moved toward each other to penetrate the skin surrounding the wound; and
   means angularly urging said first and second arms about said interconnecting means toward said closed position whereby said free ends of said first and second arm skin-engaging members are urged toward each other when said skin-engaging members penetrate the skin to facilitate healing of the wound.

2. A wound closing device as recited in claim 1 wherein said first and second arms are substantially planar.

3. A wound closing device as claimed in claim 2 wherein said skin-engaging members extend toward said interconnecting means.

4. A wound closing device as recited in claim 2 wherein said first and second arms define an angle of about 170° to about 190° when said first and second arms are in said closed position.

5. A wound closing device as recited in claim 1 and further comprising bandage means attached to said first and second arms for covering the wound.

6. A wound closing device as recited in claim 5 wherein said bandage means includes at least one adhesive surface for retaining said bandage means on skin.

7. A wound closing device as recited in claim 5 wherein said bandage means carries a beneficial, body-treating composition.

8. A wound closing device as recited in claim 1 wherein said urging means also urges said first and second arms to said open position when said first and second arms are moved a predetermined distance toward said open position.

9. A wound closing device as recited in claim 1 wherein said first and second arms carry a beneficial, body-treating composition.

10. A wound closing device as recited in claim 1 wherein said skin-engaging members carry a beneficial, body-treating composition.

11. A wound closing device as recited in claim 1 wherein said first and second arms have an adhesive surface for retaining said first and second arms on the skin.

12. A wound closing device as recited in claim 1 wherein said first arm, said second arm and said interconnecting means are integrally formed of a single strip of material.

13. A wound closing device as recited in claim 12 wherein said strip of material is spring-like to define said urging means.

14. A wound closing device as recited in claim 13 wherein said skin-engaging members are integrally formed with said first and second arms.

15. A wound closing device as recited in claim 1 wherein said skin-engaging members have curved configurations.

16. A wound closing device as recited in claim 1 wherein at least one of said skin-engaging members is hollow whereby medication can be introduced into a wound through said at least on hollow skin-engaging member.

17. A wound closing device as recited in claim 1 and further comprising means for limiting angular movement of said arms toward said open position.

18. A wound closing device as recited in claim 17 wherein said angular movement limiting means including abutment means protruding from said first and second arms.

19. A wound closing device comprising
a strip of bendable material defining first and second arms interconnected by an intermediate portion; and
skin-engaging members extending from said first and second arms;
said strip of bendable material having a normal closed position in which said skin-engaging members penetrate the skin around a wound and are directed toward said intermediate portion and said strip of bendable material allowing movement of said first and second arms about said intermediate portion away from said normal closed position to an open position in which said skin-engaging members are spaced from each other to span a wound.

20. A wound closing device as recited in claim 19 wherein said strip of bendable material has slots therein and said skin-engaging members are formed from material from said slots.

21. A wound closing device as recited in claim 20 wherein said strip of bendable material has spring-like properties.

22. A wound closing device comprising
body means for extending across a wound including first and second movable arms adapted to be disposed on opposite sides of the wound;
at least one first skin-engaging member extending from an end connected with said first arm to a free end directed toward said second arm
at least one second skin-engaging member extending from an end connected with said second arm to a free end directed toward said first arm; and
said first and second skin-engaging members having curved configurations whereby each of said first and second skin-engaging members follows a single path when penetrating the skin and being removed from the skin in response to movement of said first and second arms.

23. A wound closing device as recited in claim 22 wherein said bendable material is plastic.

24. A wound closing device comprising
first and second arms each carrying at least one skin-engaging member for penetrating skin on opposite sides of a wound;
means interconnecting said first and second arms for being disposed over said wound to position said first and second arms on opposite sides of the wound; and
bandage means disposed at least at said interconnecting means for overlying the wound.

25. A wound closing device comprising
body means for positioning on opposing sides of a wound; and
hollow skin-engaging means extending from said body means for penetrating the skin adjacent the wound and allowing introduction of medication into the wound.

26. A wound closing device as recited in claim 25 wherein said hollow skin-engaging means has an open free distal end and an open proximal end disposed at said body means.

27. A wound closing device as recited in claim 26 and further comprising removable cap means for closing said open proximal end of said hollow skin-engaging means.

28. A wound closing device as recited in claim 25 wherein said body means includes a first arm having an inner end and an outer end, a second arm having an inner end and an outer end and means interconnecting said inner ends of said first and second arms for allowing said first and second arms to be angularly movable, and said hollow skin-engaging means includes at least one hollow skin-engaging member extending from said first arm at a position between said inner and outer ends and at least one hollow skin-engaging member extending from said second arm at a position between said inner and outer ends.

29. A wound closing device as recited in claim 28 wherein said interconnecting means urges said first and second arms to a closed position where said hollow skin-engaging members are urged toward each other.

30. A wound closing device comprising
a first arm carrying at least one skin-engaging member extending from said first arm and having a free end for penetrating the skin;
a second arm carrying at least one skin-engaging member extending from said second arm and having a free end for penetrating the skin;
means interconnecting said first and second arms for allowing angular movement thereof relative to each other between an open position where said free ends of said first and second arm skin-engaging members are spaced from each other to span a wound and a closed position where said free ends of said first and second arm skin-engaging members are moved toward each other to penetrate the skin surrounding the wound; and
means extending from said first and second arms for limiting angular movement toward said open position.

31. A wound closing device comprising
body means for extending across a wound including first and second movable arms adapted to be disposed on opposite sides of the wound;
at least one first skin-engaging member extending from an end connected with said first arm to a sharp free end directed toward said second arm; and
at least one second skin-engaging member extending from an end connected with said second arm to a sharp free end directed toward said first arm
said first and second skin-engaging members having legs extending from said body means to said free ends and said free ends extending angularly from said legs whereby said free end lock said first and second skin-engaging members in the skin.

32. A wound closing device as recited in claim 31 wherein said legs of said first and second skin-engaging members extend transversely from said first and second arms, respectively.

33. A wound closing device as recited in claim 31 wherein said legs of said first and second skin-engaging members extend angularly from said first and second arms, respectively, toward each other.

34. A wound closing device comprising
a strip of bendable material having opposing portions bendable relative to each other to assume an open curved position and a substantially flat closed position;
a plurality of skin-engaging members extending from said opposing portions to penetrate skin on opposite sides of a wound substantially simultaneously when said strip is in said curved open position and to be embedded in the skin when said strip is in said substantially flat closed position.

35. A wound closing device as recited in claim 34 wherein said bendable material has spring-like properties urging said strip to said closed position.

36. A wound closing device as recited in claim 34 and further comprising alignment means carried on said strip for aligning said wound closing device with a wound to be closed.

37. A wound closing device as recited in claim 36 wherein said alignment means includes a lateral stripe extending centrally across said strip.

38. A wound closing device as recited in claim 34 wherein said skin-engaging members are formed of legs terminating at bent sharp free ends.

39. A wound closing device as recited in claim 34 wherein said strip of bendable material is transparent.

40. A wound closing device as recited in claim 34 wherein said bendable material is rubber.

41. A wound closing device as recited in claim 34 wherein said bendable material metal.

42. A wound closing device as recited in claim 33 and further comprising means carried on said strip for indicating the edges of the wound.

43. A wound closing device as recited in claim 33 wherein said indicating means includes a lateral stripe extending across said strip.

* * * * *